US00PP26114P3

(12) United States Plant Patent
Egger

(10) Patent No.: US PP26,114 P3
(45) Date of Patent: Nov. 17, 2015

(54) ***SEDUM* PLANT NAMED 'TOUCHDOWN BREEZE'**

(50) Latin Name: ***Sedum telephium* (Syn. *Hylotelephium telephium*)**
Varietal Denomination: Touchdown Breeze

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 220 days.

(21) Appl. No.: 13/998,099

(22) Filed: Sep. 30, 2013

(65) Prior Publication Data

US 2015/0096090 P1 Apr. 2, 2015

(51) Int. Cl.
*A01H 5/00* (2006.01)
*A01H 5/02* (2006.01)

(52) U.S. Cl.
USPC ..... Plt./479
CPC ..... *A01H 5/02* (2013.01)

(58) Field of Classification Search
USPC ..... Plt./479
See application file for complete search history.

(56) References Cited

PUBLICATIONS

Greenhouse Grower. Terra Nova Nurseries Announces New Sedum Touchdown Collection Aug. 15, 2013 retrieved on Jun. 17, 2015, retrieved from the Internet at <http://www.greenhousegrower.com/varieties/terra-nova-nurseries-announces-new-sedum-touchdown-collection/> 5 pp.*

Germania Seed Company. Emerald Coast—Ornamental Grasses and Perennials, retrieved on Jun. 18, 2015, retrieved from the Internet at <https://www.germaniaseed.com/pdf/2014/722_emeraldcoast.pdf> (2013-2014) pp. 1-13.*

* cited by examiner

*Primary Examiner* — June Hwu
(74) *Attorney, Agent, or Firm* — Klarquist Sparkman, LLP

(57) ABSTRACT

A new and distinct hybrid of *Sedum* plant substantially as shown and described, with pink flowers in large inflorescences, blue green leaves with purple tints, strong red stems, orange brown carpels when the seed is developing, a multiple crown, well branched, low, mounding habit, and excellent vigor.

2 Drawing Sheets

Botanical denomination: *Sedum telephium* (Syn. *Hylotelephium telephium*).

Variety designation: 'Touchdown Breeze'.

BACKGROUND OF THE INVENTION

The present invention relates to a new and distinct cultivar of *Sedum telephium* and given the cultivar name of 'Touchdown Breeze'. *Sedum* is in the family Crassulaceae. The new cultivar is part of a planned breeding program to make short, compact, multicrown plants. The new cultivar originated from an open pollinated cross of a proprietary seedling, *Sedum* 387-3.

Compared to the seed parent, *Sedum* 387-3, the new cultivar, has a better habit and larger inflorescences.

Compared to *Sedum* 'Desert Blonde', U.S. Plant Pat. No. 24,901, the new cultivar has pink flowers rather than creamy white.

Compared to *Sedum* 'Yellow Xenox', U.S. Plant Pat. No. 21,528, the new variety is has pink flowers rather than cream, a wider habit, with more crowns from young plants (an advantage to a nursery grower as the plants fill the pots quickly).

This new and unique *Sedum* is distinguished by:

1. pink flowers in very large inflorescences,
2. blue green leaves with purple tints,
3. strong red stems,
4. orange brown carpels when the fruit is developing, 5. a multiple crown, well branched, low, mounding habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
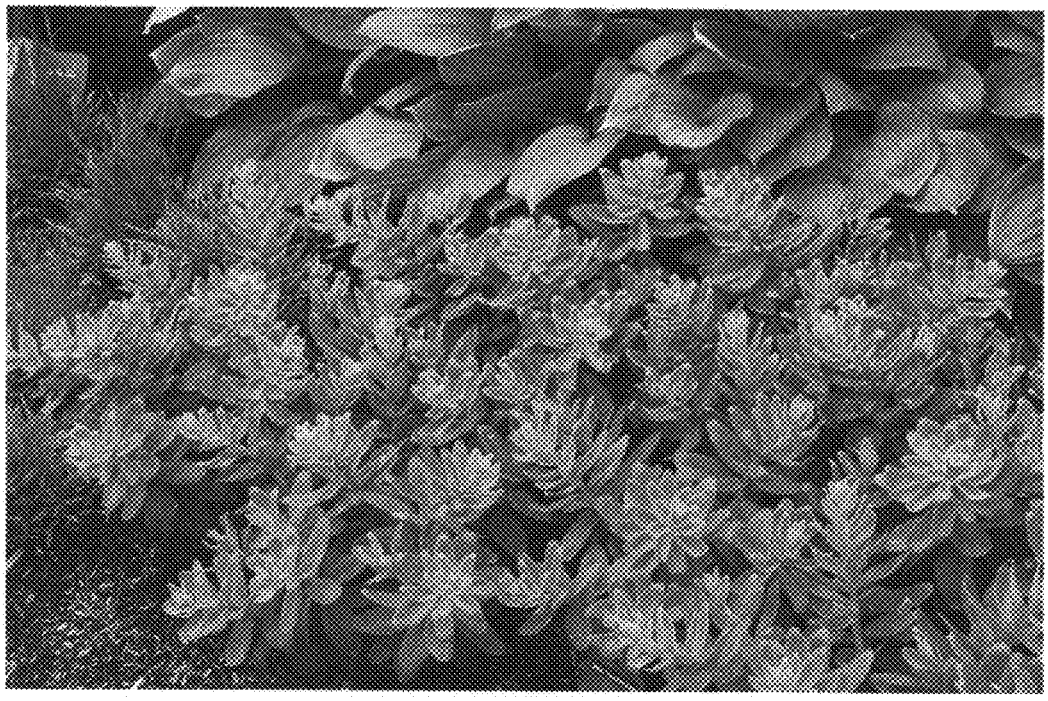
FIG. 1 shows an 18 month old *Sedum* 'Touchdown Breeze' in the garden in early July in Canby, Oreg.
Figure 2:
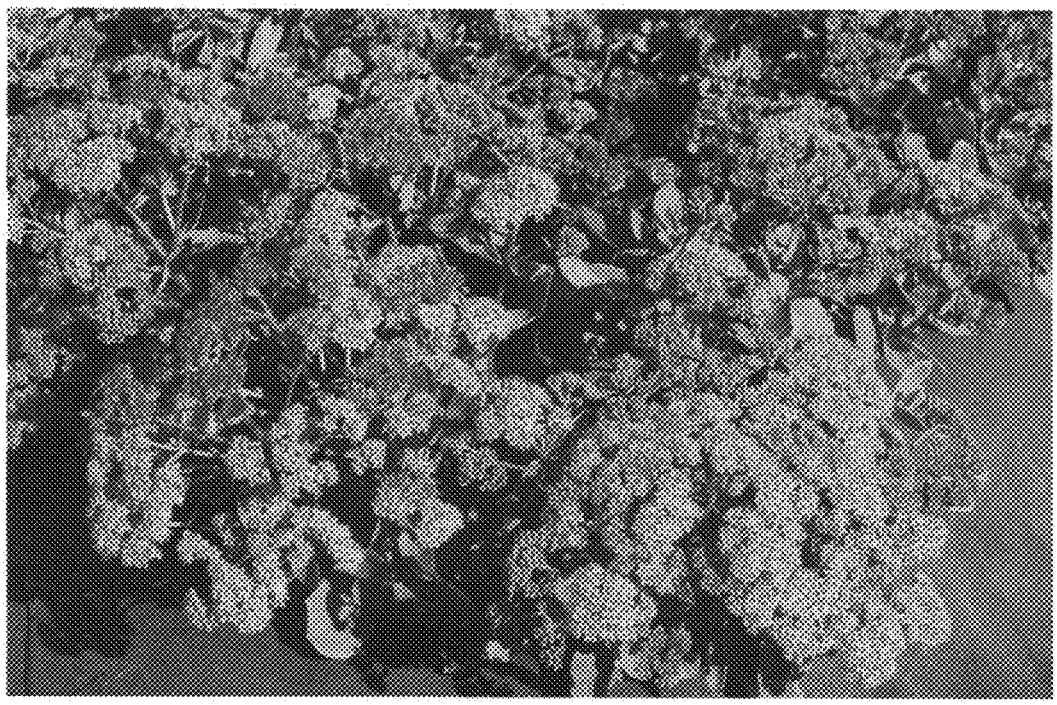
FIG. 2 shows a group of 9 month old plants of *Sedum* 'Touchdown Breeze' in bloom in the trial field in mid-September in Canby, Oreg.

The following is a detailed description of the new *Sedum* hybrid based on observations of 9 month old specimens grown in the trial bed in full sun under typical outdoor conditions in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The Royal Horticultural Society Colour Chart, $5^{th}$ edition.

Plant:

*Type*.—Herbaceous perennial.

*Hardiness*.—USDA Zone 4 to 9.

*Size*.—43 cm tall from the ground to the base of the inflorescence and 28 cm wide.

*Habit*.—Low, well branched, clumping mound.

*Vigor*.—Excellent.

Stem:

*Number*.—About 8 main stems.

*Size*.—Grows to 17 cm long and 10 mm wide.

*Internode length*.—3 cm to 5 cm long.

*Color*.—Yellow Green 144D in shade and Greyed Purple 187A in sun.

*Texture*.—Succulent.

*Surface*.—Glabrous.

Leaf:

*Type*.—Simple.

*Arrangement*.—Opposite.

*Shape*.—Ovate to oblong.

*Apex*.—Acute to obtuse.

*Base*.—Obtuse.

*Venation*.—Pinnate.

*Margins*.—Irregularly coarsely serrate.

*Blade size*.—Grows to 8.5 cm long and 5 cm wide.

*Surface*.—Glabrous on both sides.

*Texture*.—Thick, spongy, succulent.

*Petiole*.—Leaves sessile.

*Leaf color*.—Topside between Yellow Green 147A and Greyed Green 189A with the vein 138D (tinted Greyed Purple 187A on older leaves in sun); bottom side between Yellow Green 147A and Greyed Green 189A with the vein 138D.

Inflorescence:

*Type*.—Terminal, corymbose, umbel-like.

*Number of flowers*.—500 to 1000 per stem (increases with age).

*Pedicels*.—1 mm to 4 mm long, less than 1 mm wide, glabrous, Greyed Green 194B tinted Greyed Purple 187A when in sun.

*Peduncle*.—Grows to 13 cm tall and 5 mm wide, closest to Yellow Green 147C tinted Greyed Purple 187A, glabrous.

*Size of inflorescence on one branch*.—Grows to 14 cm deep and 11 cm wide.

*Bloom period*.—August through September in Canby, Oreg.

Flower bud:

*Size*.—3 mm wide, 3 mm deep.

*Description*.—Ovoid.

*Color*.—Greyed Purple 186C.

Flower:

*Type*.—Actinomorphic.

*Shape*.—Stellate.

*Size*.—5 mm deep and 8 mm wide.

*Corolla description*.—3 mm deep and 8 mm wide, 5 petals, each ovate, 5 mm long and 3 mm wide, margins entire, tip acute, glabrous on both sides, top side Red Purple 70D and bottom side Red Purple 70C.

*Calyx description*.—2 mm deep and 3 mm wide, stellate, 5 lobes, divided to the base, margins entire, tip acuminate, glabrous, Greyed Green 194B on both sides.

*Stamen description*.—10, 5 mm long, filaments 5.7 mm long and Red Purple 70D, anthers sterile and reduced, Red Purple N187A, no pollen.

*Pistil description*.—5 separate prominent carpels, each 4.5 mm deep and 2 mm wide, Red Purple 71A, style minute, stigma and style Greyed Purple 187A.

*Fragrance*.—None.

*Lastingness*.—Each stem lasts up to a month.

Fruit:

*Type*.—Ventrally dehiscent follicle, erect, attenuate.

*Fertility*.—Low.

*Size*.—3 mm wide and 4 mm deep.

*Color*.—Greyed Purple 183A.

Seed: None seen.

Disease and pest resistance or tolerance: Pest and disease resistance are typical for this type of *Sedum*. No known resistances.

I claim:

1. A new and distinct hybrid of *Sedum* plant as herein illustrated and described.

* * * * *